United States Patent [19]

Clement et al.

[11] Patent Number: 5,208,028

[45] Date of Patent: May 4, 1993

[54] GELLED EMULSION PARTICLES AND COMPOSITIONS IN WHICH THEY ARE PRESENT

[75] Inventors: Anne Clement, Paris; Pierre Fodor, Vaucresson; Gërard Guth, Montmorency, all of France; Nathalie Thiollet, Antananarivo, Madagascar

[73] Assignee: Helena Rubinstein, Inc., Wilmington, Del.

[21] Appl. No.: 330,601

[22] Filed: Mar. 29, 1989

[30] Foreign Application Priority Data

Mar. 29, 1988 [FR] France .................. 88 04105

[51] Int. Cl.⁵ .................. A61K 7/00; A61K 9/107
[52] U.S. Cl. .................. 424/401; 514/772.3; 514/772.6; 514/781; 514/782
[58] Field of Search ............. 424/401, 455; 514/940, 514/944, 772.3, 772.6, 781, 782

[56] References Cited

U.S. PATENT DOCUMENTS

| | | | |
|---|---|---|---|
| 3,563,769 | 2/1971 | Horn | 426/548 |
| 3,956,173 | 5/1976 | Towle | 252/315.3 |
| 4,401,456 | 8/1983 | Connick, Jr. | 424/488 |
| 4,767,741 | 8/1988 | Komor et al. | 424/401 X |
| 4,897,308 | 1/1990 | Vanlerbergne et al. | 514/944 |

FOREIGN PATENT DOCUMENTS

| | | |
|---|---|---|
| 0092908 | 11/1983 | European Pat. Off. . |
| 0173751 | 3/1986 | European Pat. Off. . |
| 1161005 | 6/1955 | France . |
| 2521428 | 8/1983 | France . |

*Primary Examiner*—Thurman K. Page
*Attorney, Agent, or Firm*—Ostrolenk, Faber, Gerb & Soffen

[57] ABSTRACT

The present invention relates to gelled emulsion particles obtained when predetermined volumes, especially drops, of an emulsion with an aqueous external phase, containing an appropriate reagent in solution in the said aqueous phase, are added to a gelling solution and left therein for a period of time which depends on the degree of gelling desired for the said particles. It further relates to compositions-especially solutions, gels or emulsions with an aqueous external phase-in which the said particles are present.

14 Claims, No Drawings

GELLED EMULSION PARTICLES AND COMPOSITIONS IN WHICH THEY ARE PRESENT

The present invention relates to gelled emulsion particles and to the compositions in which they are present.

According to the invention, the Applicant proposes a novel type of presentation for emulsions with an aqueous external phase. The emulsion particles according to the invention are gelled, at least partially rigidified and individualized in entities of various shapes-especially in the form of spheroidal particles-reversibly if appropriate.

This particular feature of their presentation offers numerous advantages in terms of their use.

The gelled emulsion particles according to the invention can advantageously be used in cosmetology, in pharmacy or in the agri-foodstuffs sector, according to the products which they contain.

In the remainder of the present description, the invention will be described more particularly with reference to the cosmetic sector.

To make cosmetic preparations convenient to use, or even simply for esthetic reasons, presentation in the form of capsules or spheres has already been used.

The said preparations are inside an envelope or capsule which has to be broken before they can be collected and applied.

In other cases, heterogeneous preparations have been proposed for the inclusion of one or more active ingredients in a chemically unfavorable medium or for the release of these active ingredients at the time of use. The said active ingredients are trapped in an appropriate material, which is broken by mechanical action.

Where microencapsulation is used, the effect produced on the skin is undetectable; in the case of larger capsules, the envelope remains, bringing the obvious disadvantages.

Finally, other types of cosmetic preparation exist in which spheres or drops of cream are included in a gelled and, in particular, transparent medium. This gives the preparation a novel appearance, but the included spheres cannot move without the risk of mixing with the gelled medium.

According to the invention, gelled, individualized emulsion particles are proposed which have sufficient rigidity to be included in media of variable viscosity, or even to move in media of low viscosity, without the risk of breaking and mixing. Their rigidity is sufficiently low, however, for them to be able to be used as such or introduced into a medium. Advantageously, they are introduced into a medium suitable for reducing their rigidity. They thereby gain flexibility and are capable of mixing very intimately with the said inclusion medium when the product is taken with the finger and then spread on the skin or when it passes through an appropriate system such as a pumping system.

The gelled emulsion particles according to the invention are obtained when predetermined volumes of an emulsion with an aqueous external phase, containing an appropriate reagent in solution in the said aqueous phase, are added to a gelling solution and left therein for a period of time which depends on the desired degree of gelling.

The particles according to the invention can be obtained from any emulsion with an aqueous external phase.

In the present patent application, emulsion is understood as meaning any type of emulsion with an aqueous external phase—macroemulsion or microemulsion, oil-in-water emulsion or multiple emulsion, with or without emulsifier—or any other equivalent system with an emulsifier—or any other equivalent system with an aqueous external phase, especially a disperse system.

The said emulsion contains an appropriate reagent in solution in its aqueous phase. The said reagent is at least one compound which, on contact with the gelling solution, causes at least partial rigidification of the volumes of emulsion introduced therein.

The said gelling solution contains at least one product capable of reacting with the said reagent contained in the emulsion.

The reaction involved is a reaction which instantaneously generates an insoluble material from two soluble compounds, respectively present in the emulsion with an aqueous external phase and in the gelling solution.

The emulsion particles are trapped in the structure of this insoluble compound.

The consistency of the insoluble entities obtained can obviously vary according to the nature and the concentration of the reagent in the emulsion and those of the gelling solution.

It also depends on the period of time for which the said entities, i.e. the said volumes, are left in the said gelling solution.

Different products can be obtained according to the invention by varying the said period of time:

products of the gelatin capsule type which are gelled at their periphery only, over a greater or lesser thickness; or products gelled and rigidified to the core.

These different types of particles form an integral part of the invention. However, the particles gelled to the core represent a preferred variant of the invention.

Such particles, gelled to the core, are advantageously obtained after ageing, i.e. after they have been left in contact with the gelling solution for a sufficient period of time to enable the reaction involved to reach equilibrium. Once the said equilibrium has been reached, the particles are perfectly stable.

According to different variants, the addition of the emulsion to the gelling solution can be carried out hot or cold. In particular, it is carried out hot with viscous emulsions such as creams. The size, shape and consistency of the particles can be varied by modifying numerous parameters, especially the size of the orifice of the extrusion system, the viscosity of the emulsion, its extrusion temperature, the concentration of the gelling solution, etc.

Thus spheroidal particles are obtained by adding the emulsion dropwise. This is a preferred variant of the invention.

According to other variants, it is possible to obtain filaments or other entities of various shapes.

The said entities can be collected by decantation or filtration.

They can also be kept in the solution in which they were prepared, in which case the latter advantageously contains preservatives.

The compounds which are soluble in the aqueous external phase of the emulsion and in the gelling solution and capable of generating an insoluble material on contact are preferably salts which interact by ion exchange.

The appropriate reagent in the emulsion with an aqueous external phase is advantageously selected from products having a polymeric structure and more particularly from products having a polysaccharide structure carrying acid groups, and mixtures thereof.

According to the invention, it is advantageous to use compounds selected from soluble alginates (for example sodium alginates), soluble carrageenan, soluble chitin derivatives and mixtures thereof.

Such compounds are generally present in a proportion of 0.2 to 1.5% by weight in the emulsion. In fact, the amount of reagent present depends on the nature of the latter. Thus, for example, alginates are advantageously present in a proportion of 0.3 to 0.6% and carrageenan in a proportion of about 1%.

Examples of compounds used in the gelling solution for reacting with the said products are soluble metal salts, especially alkali metal or alkaline earth metal salts or mixtures thereof. Calcium chloride, potassium chloride etc. are used in particular.

The gelling solution advantageously contains between 0.01 and 0.05 mol/l of such salts.

Those skilled in the art will know how to optimize the said concentrations—concentration of the reagent in the emulsion, concentration of the product used to react with the said reagent in the gelling solution—in order to obtain the desired result.

Thus gelled emulsion particles according to the invention can advantageously be obtained when predetermined volumes, especially drops, of an emulsion with an aqueous external phase, containing sodium alginate, are added to a solution of calcium chloride. The said particles are recovered, preferably after ageing, by decantation or filtration.

The calcium chloride and the sodium alginate are in solution. The said sodium alginate in contact with the said calcium chloride generates a salt—calcium alginate—whose structure, of the crosslinked type, causes the emulsion to solidify or, more precisely, traps the emulsion particles.

The time after which the particles are recovered is advantageously that which allows an equilibrium of calcium/sodium ions to establish between the gelling solution and the said instantaneously obtained particles. This ageing time is about 8 days.

The particles can also be recovered before this ageing time has elapsed, in which case they will be gelled to a lesser extent.

Likewise, gelled emulsion particles according to the invention are advantageously obtained when predetermined volumes, especially drops, of an emulsion with an aqueous external phase, containing carrageenan, are added to a solution of potassium chloride. The particles obtained are recovered in the same way, preferably after ageing, by decantation or filtration.

Determination of the parameters of this manipulation—concentration of salt in the gelling solution, concentration of reagent in the emulsion, presence of additives (preservatives if appropriate), total volume of emulsion transferred into the solution, volume of the said solution used, size of the predetermined volumes, residence time, etc.—is within the domain of those skilled in the art.

They will easily be able to vary the said parameters to give harder or softer particles.

As specified above, it is possible according to the invention to obtain gelled particles from any emulsion with an aqueous external phase. In particular, gelled particles can be prepared with emulsions containing amino acids such as arginine, or with emulsions containing dihydroxyacetone, or with emulsions containing vitamin C, and so on.

According to the invention, the proposed novel presentation for emulsions with an aqueous external phase improves their storage, their introduction and their preservation in another medium. Advantageously, the invention will be put into practice when it is desired to store mutually incompatible products in the same container (for simultaneous use).

The particles of the invention can be obtained with emulsions containing different types of active ingredients, for example active principles of drugs, active ingredients of cosmetics or even different raw materials in the agri-foodstuffs sector. The invention can therefore be utilized advantageously in the pharmaceutical, agri-foodstuffs or cosmetic industries.

It was indicated above that the gelled emulsion particles obtained according to the present invention can be used as such or introduced into a medium of variable viscosity, such a use being possible on account of their relative rigidity.

The invention therefore further relates to compositions, especially pharmaceutical, cosmetic or agri-foodstuffs compositions, which contain gelled emulsion particles such as described above.

The said compositions actually contain at least one of the said particles and advantageously such particles obtained from emulsions of different types.

It is in fact of particular value to use particles of the invention for storing volumes of emulsions containing different products, especially mutually incompatible products, in the same medium, in the same composition. These products can thus be stored and preserved together, without interacting, prior to use for a common purpose.

A non-limiting example which may be mentioned is the possibility, afforded by the present invention, of preparing emulsion particles containing dihydroxyacetone on the one hand and amino acids such as arginine on the other, of including these two types of product in the form of gelled particles in a medium and of preserving them therein with no observable color reaction.

The compositions containing the gelled particles of the invention can consist of solutions, gels or emulsions.

The term "emulsion" has the same meaning here as previously, i.e. any kind of emulsion, especially a dispersion, with an aqueous external phase.

The gel can be obtained from any water-dispersible gelling agent and more particularly from gelling agents having a carboxyvinylic structure (carbomers), or from acrylic polymers, carboxymethyl, ethyl or propyl celluloses or xanthan gums.

The gelled particles are introduced into the said compositions simply by mixing. Depending on the desired result, a greater or lesser amount thereof can be introduced: for example from 5 to 50% by weight or even more.

The compositions in which gelled emulsion particles of the invention are included advantageously contain a sufficient amount of a base which is capable of producing an "opposite reaction" to that which led to the gelling (rigidification) of the said particles (a reaction which renders the said particles "fragile, i.e., less rigid").

It is possible to use one base or a mixture of at least two bases.

The base is selected from bases compatible with the medium which can be used safely and are capable of generating a new, soluble compound from the insoluble gelled particles, especially a new, soluble salt from insoluble salts such as calcium alginate or potassium carrageenate. It will preferably be selected from the following list of compounds: sodium hydroxide, triethanolamine, diisopropanolamine, basic amino acids such as arginine and lysine, and mixtures thereof.

To obtain the desired result, from 0.01 to 0.1% by weight of base is generally present in the inclusion medium for the particles.

However, these figures are given by way of indication; those skilled in the art will know how to optimize the said amount of base in a particular case.

It is specified here that, in certain particular cases, the inclusion medium for the said particles may contain a much larger amount of base: thus the amount of base required to render the particles fragile can be added to a certain amount of base required to neutralize the gel used.

The reactions involved in preparing the particles of the invention and rendering them fragile are specified below, in one particular case, by way of example.

In the production of particles, it is possible to use the following reaction:

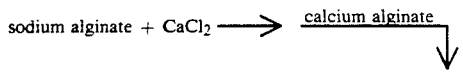

in which the emulsion particles are trapped.

If the particles containing the said calcium alginate are included in a medium containing triethanolamine (TEA), part of the calcium alginate will be converted to TEA alginate, which is a soluble salt. Consequently, the particles based on calcium alginate lose rigidity and are rendered fragile.

Therefore, when a base is present in the medium into which the gelled particles according to the invention are introduced, their rigidity is seen to decrease and the emulsion returns at least partially to its initial viscosity.

By choosing the nature of the base and determining its proportion, it is possible to ensure that the entities retain their shape and their stability in the medium, while becoming extremely flexible. They are then capable of blending into the said medium to generate a perfectly homogeneous product under any kind of mechanical action. This means in particular that no special effort is required to reconstitute a perfectly homogeneous product instantaneously when taking the mixture—medium + gelled particles within it—and spreading it on the skin.

The heterogeneous mixture—medium + gelled particles within it—can be used in a pump-action bottle. A perfectly homogeneous mixture, prepared immediately before use, is obtained simply by actuating the mechanism.

In general, such a mixture can advantageously be used in a container equipped with a dispensing system which is such that the said heterogeneous mixture becomes homogeneous on passing through the said system, the gelled emulsion particles blending into their inclusion medium.

Further advantages and characteristics of the invention will be understood more clearly from the following description of Examples of the preparation of gelled emulsion particles according to the invention and their incorporation into an appropriate medium.

I-Preparation of the emulsions

The percentages expressed below are percentages by weight.

EXAMPLE 1

Emulsion of the Milk Type

Two phases, A and B, are prepared:

| | % |
|---|---|
| A | |
| Stearic acid | 1.00 |
| Stearyl alcohol | 2.00 |
| Glyceryl isostearate | 3.50 |
| Polysorbate 60 | 1.20 |
| Sorbitan sesquiolate | 0.30 |
| Mineral oil (and) lanolin alcohol | 3.00 |
| Dimethicone | 1.00 |
| Squalane | 1.50 |
| B | |
| Glycerol | 5.00 |
| Triethanolamine | 0.20 |
| Sodium alginate | 0.50 |
| Demineralized water qs | 100.00 |
| Preservative | qs |
| C | |
| Fragrance | qs |

Phases A and B are heated to 75° C. The emulsion is prepared by pouring A into B, with stirring.

The emulsion is cooled slowly. The fragrance is added at 40° C.

EXAMPLE 2

Emulsion of the Milk Type Containing Dihydroxyacetone

Two phases, A and B, are prepared:

| | % |
|---|---|
| A | |
| Sorbitan tristearate | 0.50 |
| PEG-40 stearate | 1.25 |
| Cetyl palmitate | 3.50 |
| Glyceryl stearate | 2.00 |
| Caprylic/capric triglyceride | 6.00 |
| Dimethicone | 2.00 |
| Tocopherol | 3.00 |
| PPG-15 stearyl ether | 5.00 |
| B | |
| Glycerol | 5.00 |
| Sodium alginate | 0.40 |
| Demineralized water qs | 100.00 |
| Preservatives | qs |
| Dihydroxyacetone | 10.00 |
| C | |
| Fragrance | qs |

Phases A and B are heated to 75° C. The emulsion is prepared by pouring A into B, with stirring.

The emulsion is cooled slowly. The fragrance is added at 40° C.

EXAMPLE 3

Emulsion of the Milk Type Containing L-arginine

Two phases, A and B, are prepared:

|  | % |
|---|---|
| A | |
| Sorbitan tristearate | 0.50 |
| PEG-40 stearate | 1.25 |
| Cetyl palmitate | 3.50 |
| Glyceryl stearate | 2.00 |
| Caprylic/capric triglyceride | 6.00 |
| Dimethicone | 2.00 |
| Tocopherol | 3.00 |
| PPG-15 stearyl ether | 5.00 |
| B | |
| Glycerol | 5.00 |
| Sodium alginate | 0.40 |
| Demineralized water qs | 100.00 |
| Preservatives | qs |
| L-arginine | 10.00 |
| C | |
| Fragrance | qs |

Phases A and B are heated to 75° C.

The emulsion is prepared by pouring A into B, with stirring.

The emulsion is cooled slowly. The fragrance is added at 40° C.

EXAMPLE 4

Emulsion of the Milk Type Containing a Water-Soluble Derivative of Vitamin C

Two phases, A and B, are prepared:

|  | % |
|---|---|
| A | |
| Sorbitan tristearate | 0.50 |
| PEG-40 stearate | 1.25 |
| Cetyl palmitate | 3.50 |
| Glyceryl stearate | 2.00 |
| Caprylic/capric triglyceride | 6.00 |
| Dimethicone | 2.00 |
| PPG-15 stearyl ether | 5.00 |
| B | |
| Glycerol | 5.00 |
| Sodium alginate | 0.40 |
| Magnesium ascorbylphosphate | 3.00 |
| Demineralized water qs | 100.00 |
| Preservatives | qs |
| C | |
| Fragrance | qs |

Phases A and B are heated to 75° C.

The emulsion is prepared by pouring A into B, with stirring.

The emulsion is cooled slowly. The fragrance is added at 40° C.

EXAMPLE 5

Emulsion of the Cream Type

Two phases, A and B, are prepared:

|  | % |
|---|---|
| A | |
| PEG-30 stearate and glyceryl stearate | 6.00 |
| Stearyl alcohol | 3.00 |
| Mineral oil | 15.00 |
| B | |
| Sodium alginate | 0.40 |
| Glycerol | 3.00 |
| Triethanolamine | 0.35 |
| Carbomer 934 | 0.30 |
| Demineralized water qs | 100.00 |
| Preservatives | qs |
| C | |
| Fragrance | qs |

Phases A and B are heated to 80° C.

The emulsion is prepared by pouring A into B, with stirring.

The emulsion is left to cool to 50° C. before the fragrance is added.

The emulsion is kept at 50° C. and used at this temperature, in view of its viscosity, for pouring into the gelling solution (see below).

EXAMPLE 6

Emulsion of the Cream Type

Two phases, A and B, are prepared:

|  | % |
|---|---|
| A | |
| Sorbitan tristearate | 0.50 |
| PEG-40 stearate | 1.25 |
| Cetyl palmitate | 3.00 |
| Glyceryl monostearate (self-emulsifying) | 3.50 |
| Mineral oil | 16.00 |
| B | |
| Carrageenan | 1.00 |
| Glycerol | 5.00 |
| Demineralized water qs | 100.00 |
| Preservatives | qs |
| C | |
| Fragrance | qs |

Phases A and B are heated to 80° C.

The emulsion is prepared by mixing them, with stirring.

The fragrance is added at 50° C.

The emulsion is kept at 50° C. and used at this temperature, in view of its viscosity, for pouring into the gelling solution (see below).

II-Preparation of the gelling solution

| Process using calcium chloride | |
|---|---|
| Calcium chloride | 3.33 g |
| Water qs | 1000 g |
| Process using potassium chloride | |
| potassium chloride | 3.70 g |
| Water qs | 1000 g |

III-Preparation of the gel into which the gelled emulsion particles according to the invention are introduced

| Process using a carboxyvinylic polymer | |
|---|---|
| Carbomer 840 | 0.60 g |
| Triethanolamine qs | pH 6.5 |
| Water and preservatives qs | 100 g |
| Process using an acrylic polymer | |
| Acrylate/steareth 20 | 3.00 g |
| PEG-20 | 5.00 g |
| Imidazolidinylurea | 0.30 g |
| Triethanolamine | 0.30 g |
| Water qs | 100.00 g |

IV-Extrusion of the particles

The emulsions of Examples 1 to 6 above are introduced dropwise into the gelling solution.

The emulsions of Examples 1 to 5 are introduced into the gelling solution containing calcium chloride; the emulsion of Example 6 is introduced into the gelling solution containing potassium chloride.

This dropwise introduction is carried out using a container equipped with a system of multiple orifices, provided the rate of introduction into the gelling solution is constant, which is a condition for obtaining particles of identical dimensions.

The operation is carried out in the cold (room temperature) for emulsions of the milk type. If a cream is used, heat (50° C.) has to be applied in order to adjust the viscosity.

This operation is described in greater detail below for the case of any one of the emulsions of Examples 1 to 5, by way of illustration.

200 ml of an emulsion are run dropwise into 300 ml of a solution of calcium chloride containing 0.03 mol/l.

At equilibrium—after 8 days—the equivalent concentration of calcium ions in the particles and in the solution is equal to 0.018 mol/l. Under these conditions, the particles have a stable rigidity and can be kept in the solution in which they were prepared, if the latter contains preservatives.

If appropriate, the resulting emulsion particles are introduced into the gel.

For example, 20% by weight thereof can be introduced.

They are introduced into the gel (carboxyvinylic or acrylic polymer containing triethanolamine) after rinsing with demineralized water.

Homogeneity is achieved by means of slow stirring; this can be carried out using any type of mixer provided with an anchor or a planetary system enabling the speed of rotation to be adjusted.

Gelled particles, according to the invention, obtained from the emulsions of Examples 2 and 3 above were included in the same gel.

No coloration is observed.

The active ingredients do not react with one another, even after several days of accelerated ageing in an oven at 45° C.

A reference product containing amino acid and dihydroxyacetone, on the other hand, very rapidly develops a coloration.

The gelled particles according to the invention can therefore be used to prepare a very stable self-tan product. The said product is actually prepared by the user immediately before use, the active products being mixed by mechanical action.

What is claimed is:

1. A composition comprising (a) particles of gelled emulsion, said particles produced by adding discrete volumes of at least one emulsion to a gelling solution, said emulsion containing at least one active ingredient and having an aqueous external phase containing in solution therein a soluble reagent which produces gelling at least at the peripheries of said discrete volumes upon reaction with said gelling solution, and (b) a medium containing a sufficient amount of base to decrease the rigidity of said particles of gelled emulsion, said particles being contained in said medium.

2. A composition according to claim 1 wherein said medium is a solution, gel or emulsion.

3. A composition according to claim 1 wherein said base is selected from the group consisting of sodium hydroxide, triethoxylamine, diisopropylamine, basic aminoacids and mixtures thereof.

4. A composition according to claim 3 wherein said base is triethanolamine.

5. A composition according to claim 1 wherein said soluble reagent comprises at least one compound having a saccharide structure carrying acid groups.

6. A composition according to claim 5 wherein said compound having a saccharide structure is selected from the group consisting of alginates, carrageenans, chitin derivatives and mixtures thereof.

7. A composition according to claim 1 wherein said gelling solution is an aqueous solution of at least one metal salt.

8. A composition according to claim 7 wherein said metal salt is an alkali metal or alkaline earth metal salt.

9. A composition according to claim 7 wherein said salt is calcium chloride or potassium chloride.

10. A composition according to claim 2 wherein said medium is a gel obtained from a water-dispersible gelling agent selected from the group consisting of gelling agents having a carboxyvinylic structure, acrylic polymers, carboxymethyl, carboxyethyl and carboxypropyl cellulose and xanthan gums.

11. A composition according to claim 1 wherein said at least one active ingredient is an active cosmetic ingredient.

12. A composition according to claim 11 wherein said cosmetic ingredient is selected from the group consisting of dihydroxy acetone, amino acids and vitamin C.

13. A composition according to claim 1 wherein said particles of gelled emulsion are obtained from at least two emulsions containing different active ingredients.

14. A composition according to claim 2 wherein said medium is a gel containing triethanolamine, and said particles of gelled emulsion comprise particles containing dihydroxyacetone and particles containing L-arginine.

* * * * *